(12) United States Patent
Kajikawa

(10) Patent No.: US 8,217,182 B2
(45) Date of Patent: Jul. 10, 2012

(54) PROCESS FOR PRODUCING CYCLIC N-HYDROXY IMIDE COMPOUNDS

(75) Inventor: Yasuteru Kajikawa, Himeji (JP)

(73) Assignee: Daicel Chemical Industries, LTD., Sakai-shi (JP)

( * ) Notice: Subject to any disclaimer, the term of this patent is extended or adjusted under 35 U.S.C. 154(b) by 182 days.

(21) Appl. No.: 12/510,393

(22) Filed: Jul. 28, 2009

(65) Prior Publication Data

US 2009/0286993 A1 Nov. 19, 2009

Related U.S. Application Data

(62) Division of application No. 11/547,749, filed as application No. PCT/JP2005/005701 on Mar. 28, 2005, now Pat. No. 7,582,774.

(30) Foreign Application Priority Data

May 17, 2004 (JP) ................. 2004-147041

(51) Int. Cl.
*A61K 31/395* (2006.01)
*A61K 31/35* (2006.01)
*C07D 201/00* (2006.01)
*C07D 307/02* (2006.01)
*C07D 309/02* (2006.01)

(52) U.S. Cl. ........ 548/452; 514/412; 514/425; 514/460; 514/470; 514/473; 548/543; 549/232; 549/233; 549/240

(58) Field of Classification Search ............ 514/412, 514/425, 460, 470, 473; 548/452, 543; 549/232, 549/233, 240
See application file for complete search history.

(56) References Cited

U.S. PATENT DOCUMENTS

| | | | |
|---|---|---|---|
| 5,079,331 A | 1/1992 | Kitahara et al. | |
| 5,426,190 A | 6/1995 | Govindan et al. | |
| 5,493,031 A * | 2/1996 | Govindan | 548/542 |
| 5,616,586 A | 4/1997 | Nagata et al. | |
| 6,316,639 B1 * | 11/2001 | Fritz-Langhals | 548/542 |
| 2004/0029862 A1 | 2/2004 | Belanger et al. | |

FOREIGN PATENT DOCUMENTS

| | | |
|---|---|---|
| JP | 61-246180 A | 11/1986 |
| JP | 3-41067 A | 2/1991 |
| JP | 4-46155 A | 2/1992 |
| JP | 7-500591 A | 1/1995 |
| JP | 8-92209 A | 4/1996 |
| JP | 8-119939 A | 5/1996 |
| JP | 2001-233854 A | 8/2001 |
| JP | 2001233854 A * | 8/2001 |
| JP | 3288682 B2 | 3/2002 |
| JP | 2003-528076 A | 9/2003 |
| JP | 2004-51626 A | 2/2004 |
| JP | 2004051626 A * | 2/2004 |

OTHER PUBLICATIONS

European Patent Office Supplementary Search Report issued Mar. 19, 2010 in EP Application No. 05727160.3.
Office Action issued May 21, 2008, in parent U.S. Appl. No. 11/547,749.
Office Action issued Oct. 29, 2008, in parent U.S. Appl. No. 11/547,749.
Office Action issued Jul. 28, 2009, in parent U.S. Appl. No. 11/547,749.

* cited by examiner

*Primary Examiner* — Kamal Saeed
*Assistant Examiner* — Janet L Coppins
(74) *Attorney, Agent, or Firm* — Birch, Stewart, Kolasch & Birch, LLP

(57) ABSTRACT

A cyclic polycarboxylic acid anhydride, a polycarboxylic acid, or a mixture of them is allowed to react with hydroxylamine or a salt thereof in an organic solvent under dewatering conditions to yield a corresponding cyclic N-hydroxyimide compound. The cyclic polycarboxylic acid anhydride can be, for example, succinic anhydride or glutaric anhydride. The polycarboxylic acid can be, for example, succinic acid, glutaric acid, or adipic acid. In this process, the reaction is preferably carried out using an organic solvent capable of undergoing azeotropy with water as all or part of a reaction solvent while removing water from the reaction system by azeotropy with the organic solvent. This process produces a cyclic N-hydroxyimide compound in a good yield from any of a cyclic polycarboxylic acid anhydride and a polycarboxylic acid.

11 Claims, 1 Drawing Sheet

[FIG. 1]
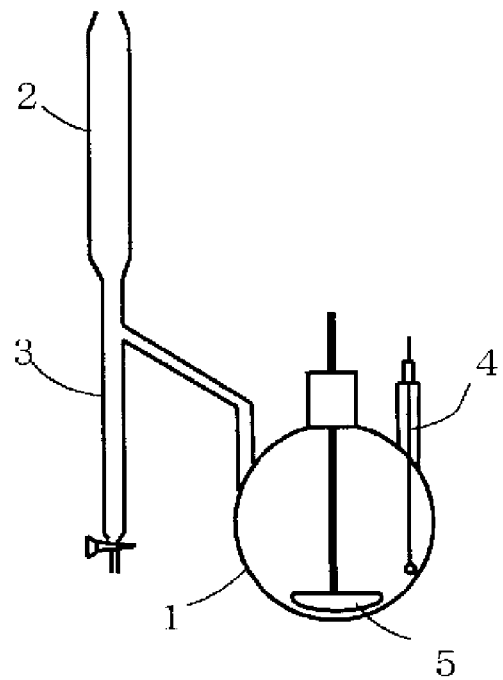
[FIG. 2]
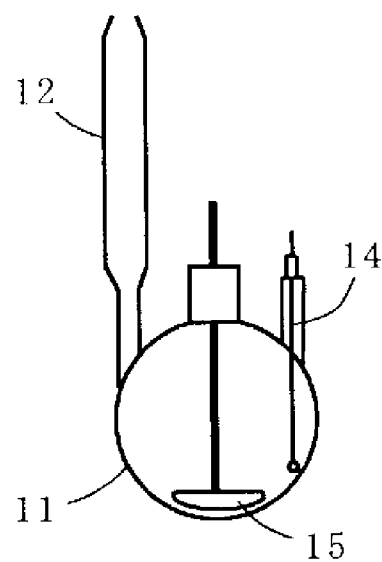

PROCESS FOR PRODUCING CYCLIC N-HYDROXY IMIDE COMPOUNDS

CROSS-REFERENCE TO RELATED APPLICATIONS

This application is a 37 CFR §1.53(b) divisional of U.S. application Ser. No. 11/547,749 filed Oct. 6, 2006, now U.S. Pat. No. 7,582,774 which claims priority on PCT International Application No. PCT/JP2005/005701 filed Mar. 28, 2005, which in turn claims priority on Japanese Patent Application No. 2004-147041 filed May 17, 2004. The entire contents of each of these application is hereby incorporated by reference.

TECHNICAL FIELD

The present invention relates to processes for producing cyclic N-hydroxyimide compounds. More specifically, it relates to processes for producing a corresponding cyclic N-hydroxyimide compound by allowing a polycarboxylic acid or a cyclic acid anhydride thereof to react with hydroxylamine or a salt thereof. Such cyclic N-hydroxyimide compounds are useful typically as oxidizing agents for use in developers for photographs, reagents for synthetically preparing peptides, oxidizing catalysts, intermediates for synthetically preparing insecticides, and initiators for polymerization reactions.

BACKGROUND ART

Widely known processes for producing cyclic N-hydroxyimide compounds are processes of allowing a cyclic acid anhydride to react with hydroxylamine. Japanese Unexamined Patent Application Publication No. 2001-233854 discloses a process of producing a cyclic N-hydroxyimide compound by allowing a cyclic acid anhydride to react with hydroxylamine in a carboxylic acid solvent. This process, however, cannot be said to be industrially satisfactory, since the yield of the cyclic N-hydroxyimide compound on the basis of the cyclic acid anhydride is as low as 60% to 70%. Japanese Patent No. 3288682 discloses a process of producing a cyclic N-hydroxyimide compound by allowing a cyclic acid anhydride to react with a hydroxylamine salt in a solvent without adding a base. The yield of the cyclic N-hydroxyimide compound according to this process significantly varies from 40% to 90%, and a higher yield is achieved when the hydroxylamine salt is used in an amount of about two times by mole that of the cyclic acid anhydride.

As is described above, the conventional processes of producing a cyclic N-hydroxyimide compound by the reaction between a cyclic acid anhydride and hydroxylamine show low yields of the cyclic N-hydroxyimide compound on the bases of the cyclic acid anhydride and offer low utilization rates of the cyclic acid anhydride. A possible solution to improve this is recovery and reuse of unreacted cyclic acid anhydride, but this invites extra cost typically for facilities for recovery and is economically disadvantageous. The yield of the cyclic N-hydroxyimide compound is increased by using an excess amount of hydroxylamine to the cyclic acid anhydride, but this invites a decreased utilization rate of hydroxylamine and is also economically disadvantageous.

Most processes for producing cyclic N-hydroxyimide compounds described in documents use a cyclic acid anhydride, but few employ a dicarboxylic acid, as a raw material component to be reacted with hydroxylamine or a salt thereof. Consequently, it is substantially impossible to yield a cyclic N-hydroxyimide compound from a dicarboxylic acid which is resistant to conversion into a cyclic acid anhydride. Even in the case of a dicarboxylic acid being readily converted into a cyclic acid anhydride, demands have been made to provide a process of producing a cyclic N-hydroxyimide compound directly from the dicarboxylic acid, bypassing a cyclic acid anhydride. This process avoids the step of converting the dicarboxylic acid into a cyclic acid anhydride and is economically very advantageous typically in plant cost.

Patent Document 1: Japanese Unexamined Patent Application Publication No. 2001-233854
Patent Document 2: Japanese Patent No. 3288682

DISCLOSURE OF INVENTION

Problems to be Solved by the Invention

Accordingly, an object of the present invention is to provide a process for producing cyclic N-hydroxyimide compounds in good yields from any of cyclic polycarboxylic acid anhydrides and polycarboxylic acids.

Another object of the present invention is to provide a process for producing cyclic N-hydroxyimide compounds with a high utilization rate of the raw material component.

Means for Solving the Problems

After intensive investigations to achieve the objects, the present inventors have found that a corresponding cyclic N-hydroxyimide compound can be produced in a good yield by allowing a cyclic polycarboxylic acid anhydride or a polycarboxylic acid to react with hydroxylamine or a salt thereof while removing water from the reaction system. The present invention has been achieved based on these findings.

Specifically, the present invention provides a process for producing cyclic N-hydroxyimide compounds, comprising the step of allowing a cyclic polycarboxylic acid anhydride, a polycarboxylic acid, or a mixture of them to react with hydroxylamine or a salt thereof in an organic solvent while carrying out dewatering to thereby yield a corresponding cyclic N-hydroxyimide compound.

The cyclic polycarboxylic acid anhydride includes a compound represented by following Formula (1):

[Chemical Formula 1]

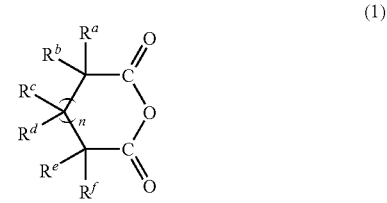

(1)

wherein $R^a$, $R^b$, $R^c$, $R^d$, $R^e$ and $R^f$ are the same as or different from one another and each represents hydrogen atom, a halogen atom, an alkyl group, a haloalkyl group, an aryl group, an aralkyl group, a cycloalkyl group, hydroxyl group, an alkoxy group, carboxyl group, a substituted oxycarbonyl group, a substituted or unsubstituted carbamoyl group, an acyl group, an acyloxy group, sulfo group, a substituted oxysulfonyl group, a substituted or unsubstituted sulfamoyl group, nitro group, a substituted or unsubstituted amino group, a substituted or unsubstituted phosphono group, or a substituted or unsubstituted phosphonooxy group, where at least two of $R^a$, $R^b$, $R^c$, $R^d$, $R^e$ and $R^f$ may be combined to form a double bond with an adjacent carbon-carbon bond or to form an aromatic or non-aromatic ring with an adjacent carbon atom or carbon chain, and where the compound may have two or more cyclic acid anhydride skeletons per molecule; and n denotes 0, 1 or 2.

The cyclic polycarboxylic acid anhydride can be, for example, at least one compound selected from succinic anhydride, glutaric anhydride, phthalic anhydride, trimellitic anhydride, pyromellitic monoanhydride, pyromellitic dianhydride, 1,8-naphthalenedicarboxylic anhydride, 2,3-naphthalenedicarboxylic anhydride, 1,4,5,8-naphthalenetetracarboxylic monoanhydride, 1,4,5,8-naphthalenetetracarboxylic dianhydride, 2,3,6,7-naphthalenetetracarboxylic monoanhydride, and 2,3,6,7-naphthalenetetracarboxylic dianhydride.

The polycarboxylic acid includes a compound represented by following Formula (2):

[Chemical Formula 2]

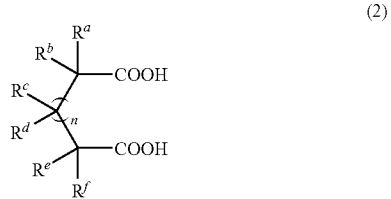

(2)

wherein $R^a$, $R^b$, $R^c$, $R^d$, $R^e$ and $R^f$ are the same as or different from one another and each represents hydrogen atom, a halogen atom, an alkyl group, a haloalkyl group, an aryl group, an aralkyl group, a cycloalkyl group, hydroxyl group, an alkoxy group, carboxyl group, a substituted oxycarbonyl group, a substituted or unsubstituted carbamoyl group, an acyl group, an acyloxy group, sulfo group, a substituted oxysulfonyl group, a substituted or unsubstituted sulfamoyl group, nitro group, a substituted or unsubstituted amino group, a substituted or unsubstituted phosphono group, or a substituted or unsubstituted phosphonooxy group, where at least two of $R^a$, $R^b$, $R^c$, $R^d$, $R^e$ and $R^f$ may be combined to form a double bond with an adjacent carbon-carbon bond or to form an aromatic or non-aromatic ring with an adjacent carbon atom or carbon chain, and where the compound may have two or more pairs of carboxyl groups capable of forming a cyclic imide skeleton per molecule; and n denotes 0, 1 or 2.

The polycarboxylic acid can be, for example, at least one compound selected from succinic acid, glutaric acid, adipic acid, phthalic acid, trimellitic acid, pyromellitic acid, 1,8-naphthalenedicarboxylic acid, 2,3-naphthalenedicarboxylic acid, 1,4,5,8-naphthalenetetracarboxylic acid, and 2,3,6,7-naphthalenetetracarboxylic acid.

In the production process, it is preferred that an organic solvent capable of undergoing azeotropy with water is used as all or part of a reaction solvent and the reaction is carried out while removing water from the reaction system by azeotropy with the organic solvent. In this case, the azeotropic distillate can be recycled to the reaction system, after removing water therefrom. The organic solvent can be, for example, at least one solvent selected from carboxylic acids, esters, ketones, aliphatic hydrocarbons, alicyclic hydrocarbons, aromatic hydrocarbons, alcohols, and halogenated hydrocarbons.

The reaction in the production process is also preferably carried out while continuously or intermittently adding an aqueous hydroxylamine solution to the reaction system.

The production process can include a first step of allowing a cyclic polycarboxylic acid anhydride, a polycarboxylic acid, or a mixture of them to react with hydroxylamine or a salt thereof in an organic solvent for predetermined time without dewatering, and a second step of carrying out the reaction while conducting dewatering. This embodiment is specifically useful in the case where the organic solvent is a solvent capable of forming a dehydration-condensation product with hydroxylamine, such as a monocarboxylic acid having one to eight carbon atoms.

Advantages

According to the present invention, cyclic N-hydroxyimide compounds can be produced in good yields from any of cyclic polycarboxylic acid anhydrides and polycarboxylic acids, and the utilization rates of raw material components can be significantly improved.

BRIEF DESCRIPTION OF THE DRAWINGS

FIG. 1 is a schematic diagram showing a reactor used in EXAMPLES 1 to 6.
FIG. 2 is a schematic diagram showing a reactor used in COMPARATIVE EXAMPLES 1 to 5.

REFERENCE NUMERALS

1,11 flask
2,12 reflux condenser
3 Dean-Stark fractionating unit
4,14 thermometer
5,15 mixing impeller

BEST MODE FOR CARRYING OUT THE INVENTION

Cyclic Polycarboxylic Acid Anhydride, and Polycarboxylic Acid

According to the present invention, a cyclic polycarboxylic acid anhydride, a polycarboxylic acid, or a mixture of them (for example, a mixture of a cyclic polycarboxylic acid anhydride with a corresponding polycarboxylic acid) is used as one of the raw material components. Each of such cyclic polycarboxylic acid anhydrides and polycarboxylic acids can be used in combination as a mixture. When there are optical isomers in the cyclic polycarboxylic acid anhydrides and polycarboxylic acids, it is possible to use one optical isomer alone or a mixture of plural different optical isomers.

The cyclic polycarboxylic acid anhydride is not specifically limited, as long as it is a compound having at least one cyclic acid anhydride skeleton per molecule. Such cyclic polycarboxylic acid anhydrides are generally represented by following Formula (I):

[Chemical Formula 3]

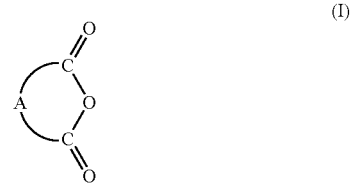

(I)

wherein A is a bivalent organic group having two or more atoms in its principal chain.

The polycarboxylic acid is not specifically limited, as long as it is a compound having at least one pair of carboxyl groups (two carboxyl groups) capable of forming a cyclic imide skeleton per molecule. Such polycarboxylic acids are generally represented by following Formula (II):

[Chemical Formula 4]

(II)

wherein A is as defined above.

Examples of the bivalent organic group in A are bivalent hydrocarbon groups such as alkylene groups, alkenylene groups, arylene group, and bivalent alicyclic hydrocarbon groups; and bivalent groups each comprising two or more of these groups with or without the interposition of a linkage group such as oxygen atom or sulfur atom.

Examples of the alkylene group are straight- or branched-chain alkylene groups each having about one to about twenty carbon atoms, such as methylene, ethylene, propylene, trimethylene, tetramethylene, pentamethylene, and hexamethylene groups, of which those having about one to about twelve carbon atoms are preferred, and those having about two to about four carbon atoms are more preferred. Examples of the alkenylene group are straight- or branched-chain alkenylene groups each having about two to about twenty, such as vinylene, and propenylene groups, of which those having about two to about twenty carbon atoms are preferred, and those having about two to about four carbon atoms are more preferred. Examples of the arylene group are o-phenylene, and 1,8-naphthylene groups. The bivalent alicyclic hydrocarbon groups include, for example, cycloalkylene groups such as 1,2-cyclopentylene and 1,2-cyclohexylene groups; cycloalkenylene groups such as 1-cyclohexen-1,2-ylene and 4-cyclohexen-1,2-ylene groups; and bivalent polycyclic alicyclic groups (bridged groups) such as decalin-2,3-ylene, decalin-1,8-ylene, norborn-2,3-ylene, and norbornen-5,6-ylene groups.

These bivalent hydrocarbon groups such as alkylene groups may each have one or more substituents. Examples of the substituents are a halogen atom, an alkyl group, a haloalkyl group, an aryl group, an aralkyl group, a cycloalkyl group, hydroxyl group, an alkoxy group, carboxyl group, a substituted oxycarbonyl group, a substituted or unsubstituted carbamoyl group, an acyl group, an acyloxy group, sulfo group, a substituted oxysulfonyl group, a substituted or unsubstituted sulfamoyl group, nitro group, a substituted or unsubstituted amino group, a substituted or unsubstituted phosphono group, and a substituted or unsubstituted phosphonooxy group.

The halogen atom includes iodine, bromine, chlorine and fluorine atoms. Examples of the alkyl group are straight- or branched-chain alkyl groups having about one to about thirty carbon atoms, and preferably about one to about twenty carbon atoms, such as methyl, ethyl, propyl, isopropyl, butyl, isobutyl, s-butyl, t-butyl, hexyl, decyl, dodecyl, tetradecyl, and hexadecyl groups. Examples of the haloalkyl group are straight- or branched-chain haloalkyl groups each having about one to about thirty carbon atoms, and preferably about one to about twenty carbon atoms, such as chloromethyl, and trifluoromethyl groups.

The aryl group includes, for example, phenyl, tolyl, xylyl, and naphthyl groups. The aralkyl group includes, for example, benzyl, 2-phenylethyl, and 1-phenylethyl groups. The cycloalkyl group includes, for example, cyclopentyl and cyclohexyl groups. The alkoxy group includes, for example, alkoxy groups each having about one to about thirty carbon atoms, and preferably about one to about twenty carbon atoms, such as methoxy, ethoxy, isopropoxy, butoxy, t-butoxy, hexyloxy, octyloxy, decyloxy, dodecyloxy, tetradecyloxy, and octadecyloxy groups.

The substituted oxycarbonyl group includes, for example, $C_{1-30}$ alkoxy-carbonyl groups such as methoxycarbonyl, ethoxycarbonyl, isopropoxycarbonyl, butoxycarbonyl, t-butoxycarbonyl, hexyloxycarbonyl, decyloxycarbonyl, and hexadecyloxycarbonyl groups, of which $C_{1-20}$ alkoxy-carbonyl groups are preferred; cycloalkyloxycarbonyl groups such as cyclopentyloxycarbonyl, and cyclohexyloxycarbonyl groups, of which 3- to 20-membered cycloalkyloxycarbonyl groups are preferred; aryloxycarbonyl groups such as phenyloxycarbonyl, and naphthyloxycarbonyl groups, of which $C_{6-20}$ aryloxy-carbonyl groups are preferred; aralkyloxycarbonyl groups such as benzyloxycarbonyl group, of which $C_{7-21}$ aralkyloxy-carbonyl groups are preferred; metalloxycarbonyl groups (carboxyl group converted into a metallic salt) such as sodiooxycarbonyl group.

The substituted or unsubstituted carbamoyl group includes, for example, carbamoyl; N-(hydrocarbon group)-substituted carbamoyl groups and N,N-di(hydrocarbon group)-substituted carbamoyl groups, such as N-methylcarbamoyl, N,N-dimethylcarbamoyl, and N-phenylcarbamoyl groups.

The acyl group includes, for example, aliphatic saturated or unsaturated acyl groups including $C_{1-30}$ aliphatic acyl groups such as formyl, acetyl, propionyl, butyryl, isobutyryl, valeryl, pivaloyl, hexanoyl, octanoyl, decanoyl, lauroyl, myristoyl, palmitoyl, and stearoyl groups, of which aliphatic $C_{1-20}$ acyl groups are preferred; acetoacetyl group; alicyclic acyl groups including cycloalkanecarbonyl groups such as cyclopentanecarbonyl and cyclohexanecarbonyl groups; and aromatic acyl groups such as benzoyl and naphthoyl groups.

The acyloxy group includes, for example, aliphatic saturated or unsaturated acyloxy groups including $C_{1-30}$ aliphatic acyloxy group such as formyloxy, acetyloxy, propionyloxy, butyryloxy, isobutyryloxy, valeryloxy, pivaloyloxy, hexanoyloxy, octanoyloxy, decanoyloxy, lauroyloxy, myristoyloxy, palmitoyloxy, and stearoyloxy groups, of which aliphatic $C_{1-20}$ acyloxy groups are preferred; acetoacetyloxy group; alicyclic acyloxy groups including cycloalkanecarbonyloxy group such as cyclopentanecarbonyloxy, and cyclohexanecarbonyloxy groups; and aromatic acyloxy groups such as benzoyloxy and naphthoyloxy groups.

The substituted oxysulfonyl group includes, for example, alkoxysulfonyl groups such as methoxysulfonyl group; cycloalkyloxysulfonyl groups such as cyclohexyloxysulfonyl group; aryloxysulfonyl groups such as phenyloxysulfonyl group; aralkyloxysulfonyl groups such as benzyloxysulfonyl group; and metalloxysulfonyl groups (sulfo group converted into a metallic salt) such as sodiooxysulfonyl group. Examples of the substituted or unsubstituted sulfamoyl group are sulfamoyl; N-(hydrocarbon group)-substituted sulfamoyl groups and N,N-di(hydrocarbon group)-substituted sulfamoyl groups, such as N-methylsulfamoyl, N,N-dimethylsulfamoyl, and N-phenylsulfamoyl groups. Examples of the substituted or unsubstituted amino group are N-(hydrocarbon group)-substituted amino groups and N,N-di(hydrocarbon group)-substituted amino groups, such as methylamino, ethylamino, dimethylamino, diethylamino, and phenylamino groups. The substituted or unsubstituted phosphono group includes, for example, phosphono; and O-(hydrocarbon group)-substituted phosphono groups such as methylphosphono, dimethylphosphono, phenylphosphono, and diphenylphosphono groups. The substituted or unsubstituted phosphonooxy group includes, for example, phosphonooxy; and O-(hydrocarbon group)-substituted phosphonooxy groups such as methylphosphonooxy, dimethylphosphonooxy, phenylphosphonooxy, and diphenylphosphonooxy groups; and O-metal-substituted phosphonooxy groups such as O,O'-disodiophosphonooxy group.

When there are plural substituents, at least two of the substituents may be combined to form an aromatic or non-aromatic ring with an atom constituting A. The aromatic or non-aromatic ring is preferably a ring having about five to about twelve members and specifically preferably a ring having about six to about ten members. The ring can be a heterocyclic ring or fused heterocyclic ring but is often a hydrocarbon ring. Examples of such rings are cycloalkane rings which may be substituted, such as cyclohexane ring; cycloalkene rings which may be substituted, such as cyclohexene ring; bridged rings including bridged hydrocarbon rings which may be substituted, such as 5-norbornene ring; and aromatic rings (including fused rings) which may be substituted, such as benzene ring and naphthalene ring. The ring often comprises an aromatic ring. The ring may have one or more substituents exemplified as the substituents which the bivalent hydrocarbon group may have, such as an alkyl group, a haloalkyl group, hydroxyl group, an alkoxy group, carboxyl group, a substituted oxycarbonyl group, an acyl group, an acyloxy group, nitro group, cyano group, amino group, and a halogen atom.

A preferred cyclic polycarboxylic acid anhydride is represented by Formula (1). A preferred polycarboxylic acid is represented by Formula (2). The same groups as above can exemplify the halogen atom, alkyl group, haloalkyl group, aryl group, aralkyl group, cycloalkyl group, alkoxy group, substituted oxycarbonyl group, substituted or unsubstituted carbamoyl group, acyl group, acyloxy group, substituted oxysulfonyl group, substituted or unsubstituted sulfamoyl group, substituted or unsubstituted amino group, substituted or unsubstituted phosphono group, and substituted or unsubstituted phosphonooxy group in $R^a$, $R^b$, $R^c$, $R^d$, $R^e$ and $R^f$ in Formulae (1) and (2).

At least two of $R^a$, $R^b$, $R^c$, $R^d$, $R^e$ and $R^f$ may be combined to form an aromatic or non-aromatic ring with an adjacent carbon atom or carbon chain. Examples of the aromatic or non-aromatic ring herein include the same aromatic or non-aromatic rings formed by at least two of substituents which the bivalent hydrocarbon group in A may have. The ring may have one or more substituents as mentioned above, such as an alkyl group, a haloalkyl group, hydroxyl group, an alkoxy group, carboxyl group, a substituted oxycarbonyl group, an acyl group, an acyloxy group, nitro group, cyano group, amino group, and a halogen atom.

Representative examples of the cyclic polycarboxylic acid anhydride are compounds represented by following Formulae (1a) to (1l):

[Chemical Formula 5]

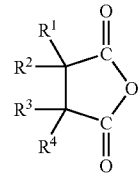

(1a)

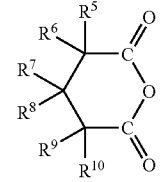

(1b)

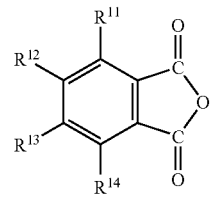

(1c)

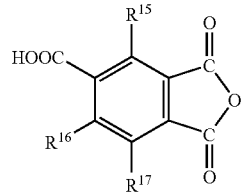

(1d)

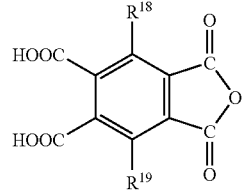

(1e)

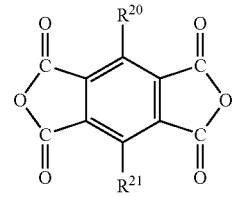

(1f)

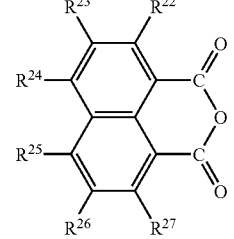

(1g)

-continued

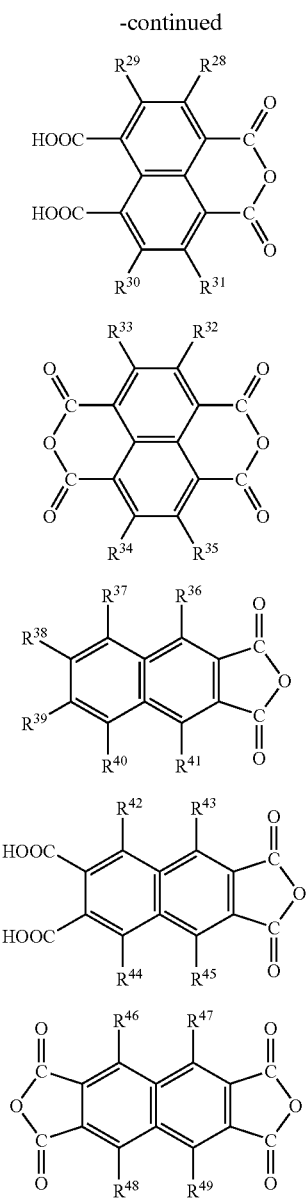

wherein each of $R^1$ to $R^{49}$ represents hydrogen atom, a halogen atom, an alkyl group, a haloalkyl group, an aryl group, an aralkyl group, a cycloalkyl group, hydroxyl group, an alkoxy group, carboxyl group, a substituted oxycarbonyl group, a substituted or unsubstituted carbamoyl group, an acyl group, an acyloxy group, sulfo group, a substituted oxysulfonyl group, a substituted or unsubstituted sulfamoyl group, nitro group, a substituted or unsubstituted amino group, a substituted or unsubstituted phosphono group, or a substituted or unsubstituted phosphonooxy group, where at least two of $R^1$ to $R^{49}$ may be combined to form a double bond with an adjacent carbon-carbon bond or to form an aromatic or nonaromatic ring with an adjacent carbon atom or carbon chain.

The same groups and rings as above can exemplify the halogen atom, alkyl group, haloalkyl group, aryl group, aralkyl group, cycloalkyl group, alkoxy group, substituted oxycarbonyl group, substituted or unsubstituted carbamoyl group, acyl group, acyloxy group, substituted oxysulfonyl group, substituted or unsubstituted sulfamoyl group, substituted or unsubstituted amino group, substituted or unsubstituted phosphono group, and substituted or unsubstituted phosphonooxy group in $R^1$ to $R^{49}$ and the aromatic or non-aromatic ring formed by at least two of $R^1$ to $R^{49}$ with an adjacent carbon atom or carbon chain in Formulae (1a) to (1l).

Specific examples of the compounds represented by Formulae (1a) to (1l) are succinic anhydride, glutaric anhydride, phthalic anhydride, trimellitic anhydride, pyromellitic monoanhydride, pyromellitic dianhydride, 1,8-naphthalenedicarboxylic anhydride, 2,3-naphthalenedicarboxylic anhydride, 1,4,5,8-naphthalenetetracarboxylic monoanhydride, 1,4,5,8-naphthalenetetracarboxylic dianhydride, 2,3,6,7-naphthalenetetracarboxylic monoanhydride, and 2,3,6,7-naphthalenetetracarboxylic dianhydride.

Representative examples of the polycarboxylic acid are compounds represented by following Formulae (2a) to (2l):

[Chemical Formula 6]

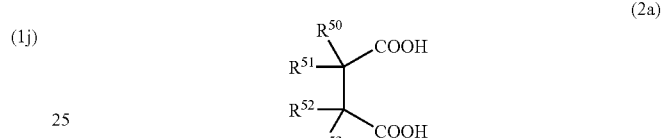

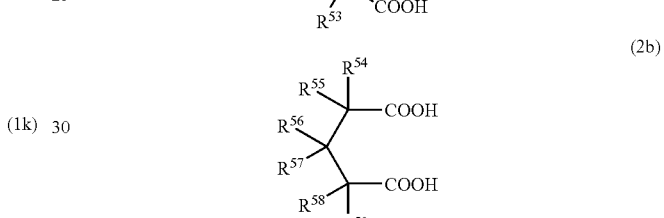

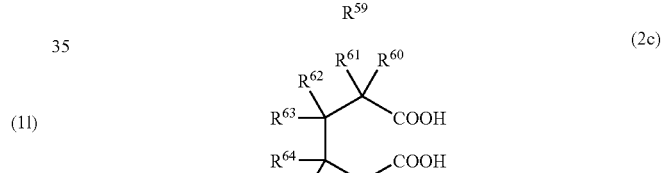

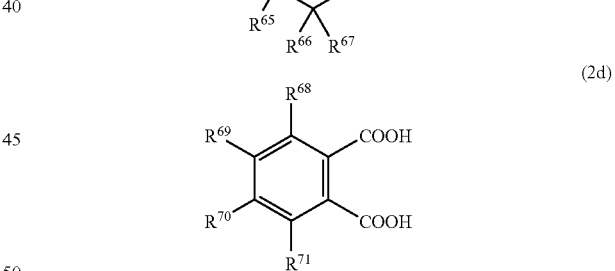

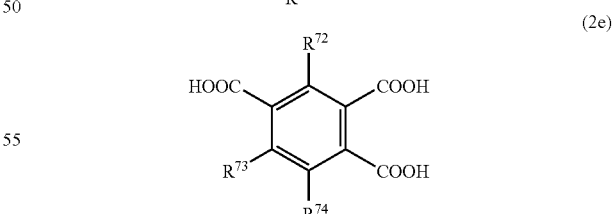

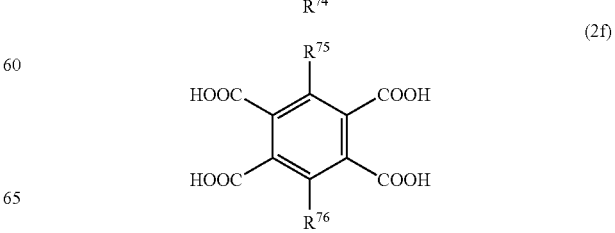

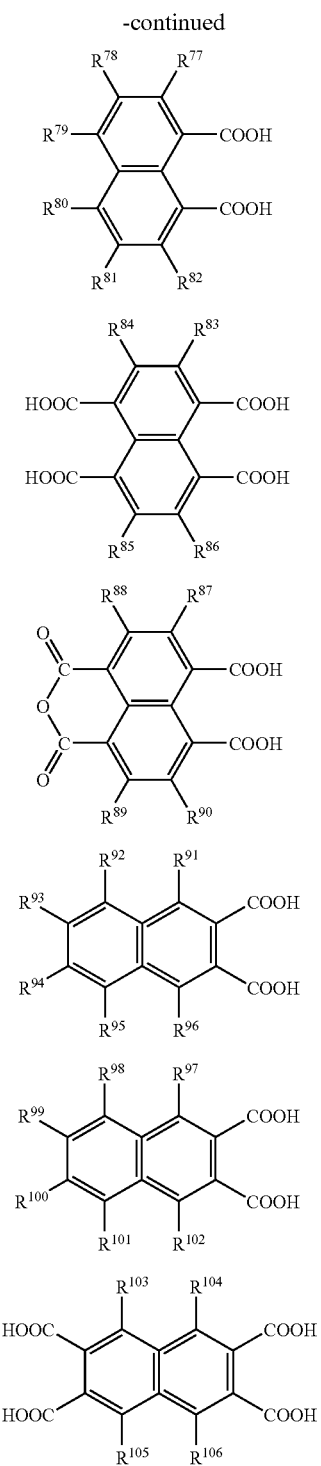

wherein each of $R^{50}$ to $R^{106}$ represents hydrogen atom, a halogen atom, an alkyl group, a haloalkyl group, an aryl group, an aralkyl group, a cycloalkyl group, hydroxyl group, an alkoxy group, carboxyl group, a substituted oxycarbonyl group, a substituted or unsubstituted carbamoyl group, an acyl group, an acyloxy group, sulfo group, a substituted oxysulfonyl group, a substituted or unsubstituted sulfamoyl group, a substituted or unsubstituted amino group, nitro group, a substituted or unsubstituted phosphono group, or a substituted or unsubstituted phosphonooxy group, where at least two of $R^{50}$ to $R^{104}$ may be combined to form a double bond with an adjacent carbon-carbon bond or to form an aromatic or non-aromatic ring with an adjacent carbon atom or carbon chain.

The same groups and rings as above can exemplify the halogen atom, alkyl group, haloalkyl group, aryl group, aralkyl group, cycloalkyl group, alkoxy group, substituted oxycarbonyl group, substituted or unsubstituted carbamoyl group, acyl group, acyloxy group, substituted oxysulfonyl group, substituted or unsubstituted sulfamoyl group, substituted or unsubstituted amino group, substituted or unsubstituted phosphono group, and substituted or unsubstituted phosphonooxy group in $R^{50}$ to $R^{106}$, and the aromatic or non-aromatic ring formed by at least two of $R^{50}$ to $R^{106}$ with an adjacent carbon atom or carbon chain in Formulae (2a) to (2l).

Specific examples of the compounds represented by Formulae (2a) to (2l) are succinic acid, glutaric acid, adipic acid, phthalic acid, trimellitic acid, pyromellitic acid, 1,8-naphthalenedicarboxylic acid, 2,3-naphthalenedicarboxylic acid, 1,4,5,8-naphthalenetetracarboxylic acid, and 2,3,6,7-naphthalenetetracarboxylic acid.

[Hydroxylamine or a Salt Thereof]

According to the present invention, hydroxylamine or a salt thereof is used as the other raw material component. Examples of the salt of hydroxylamine are salts of strong acids, such as hydrochlorides, hydrobromides, sulfates, nitrates, and phosphates. When a salt of hydroxylamine is used, the salt may be converted into free hydroxylamine or a weak acid salt of hydroxylamine by treating the salt with a base before use or in the reaction system. Examples of the base are alkali metal hydroxides such as potassium hydroxide, and sodium hydroxide; alkaline earth metal hydroxides such as magnesium hydroxide, and calcium hydroxide; alkali metal carbonates such as potassium carbonate, and sodium carbonate; alkaline earth metal carbonates such as calcium carbonate; alkali metal hydrogen carbonates such as potassium hydrogen carbonate, and sodium hydrogen carbonate; alkali metal alkoxides such as sodium methoxide and sodium ethoxide; carboxylic acid salts of alkali metals, including alkali metal acetates such as potassium acetate and sodium acetate. The amount of the base is generally 1 to 5 equivalents, preferably 1 to 2 equivalents, and more preferably 1 to 1.5 equivalents, to the salt of hydroxylamine.

Hydroxylamine or a salt thereof can be used as intact or in the form of a solution such as an aqueous solution or a dispersion. The amount of hydroxylamine or a salt thereof is generally 0.5 to 10 equivalents, preferably 1 to 2 equivalents, and more preferably 1 to 1.5 equivalents, to the acid anhydride group of the cyclic polycarboxylic acid anhydride or to the pair of carboxyl groups (pair of two carboxyl groups) capable of forming a cyclic imide skeleton of the polycarboxylic acid. When a mixture of a cyclic polycarboxylic acid anhydride and a polycarboxylic acid is used, the amount of the hydroxylamine or a salt thereof is relative to the total amount of the acid anhydride group and the pair of carboxyl groups.

[Reaction]

The reaction between a cyclic polycarboxylic acid anhydride, a polycarboxylic acid, or a mixture of them and hydroxylamine or a salt thereof is carried out in an organic solvent. Examples of the organic solvent are carboxylic acids including carboxylic acids each having about one to about twenty carbon atoms, such as formic acid, acetic acid, propionic acid, butyric acid, isobutyric acid, pentanoic acid, hexanoic acid, heptanoic acid, octanoic acid, nonanoic acid, decanoic acid, undecanoic acid, dodecanoic acid, and tetradecanoic acid; alcohols such as methanol, ethanol, and isopropyl alcohol; aromatic hydrocarbons which may be substituted, such as benzene, toluene, xylenes, and nitrobenzene; aliphatic hydrocarbons such as pentane, hexane, and heptane; alicyclic hydrocarbons which may be substituted, such as cyclohexane and methylcyclohexane; esters such as ethyl acetate and butyl acetate; ethers such as diethyl ether, dioxane, and tetrahydrofuran (THF); ketones such as ethyl methyl ketone; halogenated hydrocarbons such as carbon tetrachloride, chloroform, and methylene chloride; nitriles such as acetonitrile; amides such as N,N-dimethylformamide (DMF); and mixture of these solvents. Water can be used as a solvent for dissolving the reaction raw materials. The amount of these solvents can be selected as appropriate within ranges not adversely affecting the reaction and is usually about 10 to about 5000 parts by weight, preferably about 30 to about 2000 parts by weight, and more preferably about 50 to about 700 parts by weight, to 100 parts by weight of the total of the cyclic polycarboxylic acid anhydride and the polycarboxylic acid used in the reaction.

A significant feature of the present invention is carrying out the reaction while conducting dewatering. Water to be removed includes, for example, water used as a solvent for dissolving typically the reaction raw materials, and water by produced in reactions including neutralization reaction between a hydroxylamine salt and a base. The dewatering method is not specifically limited and includes, for example, a method of physically separating and removing water, a method of chemically removing water, and a combination of these. The method of physically separating and removing water includes (a) a method of absorbing or adsorbing water in the reaction system by arranging a substance capable of absorbing or adsorbing water in the reaction system or by allowing the reaction mixture to circulate in a column or tank filled with the substance, and (b) a method of distilling off water in the reaction system alone or by azeotropy with an organic solvent capable of undergoing azeotropy with water. The organic solvent capable of undergoing azeotropy with water can be used as all or part of the reaction solvent. The method of chemically removing water includes, for example, (c) a method of arranging a substance capable of substantially irreversibly reacting with water in the reaction system.

Examples of the substance capable of absorbing or adsorbing water for use in the method (a) are molecular sieves, silica gel, activated carbon, and high-polymer desiccants.

Examples of the organic solvent capable of undergoing azeotropy with water for use in the method (b) are carboxylic acids such as formic acid, acetic acid, propionic acid, butyric acid, isobutyric acid, and isovaleric acid; ester such as methyl chloroacetate, methyl acrylate, ethyl acetate, methyl propionate, isopropyl formate, propyl formate, butyl formate, isobutyl formate, ethyl propionate, methyl butyrate, methyl isobutyrate, propyl acetate, isopropyl acetate, diethyl carbonate, isoamyl nitrate, isoamyl formate, isobutyl acetate, butyl acetate, butyl butyrate, ethyl isobutyrate, methyl isovalerate, propyl propionate, isoamyl acetate, ethyl isovalerate, propyl butyrate, methyl caproate, propyl isobutyrate, isopropyl isobutyrate, methyl benzoate, phenyl acetate, isobutyl butyrate, isobutyl isobutyrate, benzyl acetate, ethyl benzoate, isoamylisobutyrate, methyl cinnamate, propyl benzoate, isobutyl benzoate, and isoamyl benzoate; ketones such as ethyl methyl ketone, 2-pentanone, 3-pentanone, 3-methyl-2-butanone, and 4-methyl-2-pentanone; aliphatic hydrocarbons such as hexane; alicyclic hydrocarbons such as cyclohexane; aromatic hydrocarbons such as benzene, phenol, toluene, m-xylene, and naphthalene; alcohols such as ethanol, allyl alcohol, 1-propanol, 2-propanol, 1-butanol, isobutyl alcohol, 2-butanol, tert-butyl alcohol, furfuryl alcohol, 1-pentanol, isoamyl alcohol, 2-pentanol, tert-amyl alcohol, cyclohexanol, 1-hexanol, benzyl alcohol, 1-heptanol, 1-octanol, 2-octanol, and isoamyl alcohol; halogenated hydrocarbons such as carbon tetrachloride, chloroform, methylene chloride, trichloroethylene, cis-1,2-dichloroethylene, trans-1,2-dichloroethylene, 1,2-dichloroethane, 1,2-dichloropropane, 1-chloropropane, 2-chloropropane, 1-chlorobutane, 1-chloro-2-methylpropane, and chlorobenzene; ethers such as epichlorohydrin, ethyl ether, methyl propyl ether, 1,2-dimethoxyethane, isopropyl ether, 1,2-diethoxyethane, anisole, phenetole, cineole, and phenyl ether; nitriles such as acetonitrile and acrylonitrile; aldehydes and acetals such as chloral, paraldehyde, trioxane, and safrole; sulfur-containing compounds such as carbon disulfide; nitro compounds such as nitromethane and nitrobenzene; nitrogen-containing heterocyclic compounds such as piperidine, pyridine, 3-methylpyridine, and nicotine; and phenols such as phenol.

Each of these organic solvents can be used alone or in combination. Among them, carboxylic acids, esters, ketones, aliphatic hydrocarbons, alicyclic hydrocarbons, aromatic hydrocarbons, alcohols, and halogenated hydrocarbons are typically preferred.

In the method (b), it is preferred to remove water from the azeotropic distillate and to recycle the residual organic solvent to the reaction system, for saving the amount of the organic solvent capable of undergoing azeotropy with water. In this case, the azeotropic distillate is recycled to the reaction system after removing water therefrom, for example, by bringing water in contact with a substance capable of absorbing or adsorbing water. The above-exemplified substances capable of absorbing or adsorbing water can be used herein. When the organic solvent capable of undergoing azeotropy with water is a solvent that is separated into an organic layer and an aqueous layer in its azeotropic composition, a method is also acceptable in which the azeotropic distillate is separated, the aqueous layer is removed, and the organic layer alone is recycled to the reaction system. Representative examples of the organic solvent capable of undergoing azeotropy with water and separating from water are cyclohexane, toluene, and xylenes.

Examples of the substance capable of substantially irreversibly reacting with water for use in the method (c) are chain-like acid anhydrides (noncyclic acid anhydrides) corresponding to carboxylic acids each having about one to about twelve carbon atoms, such as acetic anhydride and propionic anhydride.

From the viewpoint of the reaction rate, the reaction temperature is generally 50° C. or higher, preferably 70° C. or higher, and more preferably 90° C. or higher. In consideration of stability of the product, it is generally 200° C. or lower, preferably 180° C. or lower, and more preferably 160° C. or lower. The reaction pressure is not specifically limited. When a solvent having a low boiling point under normal pressure is used as the reaction solvent, it is preferred to pressurize the reaction system and to elevate the reaction temperature, for increasing the reaction rate.

The reaction mode can be any mode such as a batch mode, a semibatch mode and a continuous mode. In the batch mode, the raw materials, solvent and other components are placed in a reactor, followed by starting the reaction, and the reaction product is extracted after the completion of the reaction. In the semibatch mode, the reaction is carried out while continuously feeding all or part of the raw materials, solvent and other components to a reactor, and the reaction product is extracted after the completion of the reaction. In the continuous mode, the reaction is carried out while continuously feeding all or part of the raw materials, solvent and other components to a reactor, and the reaction product (reaction mixture) is continuously extracted.

Free hydroxylamine [including a weak acid salt, such as acetic acid salt of hydroxylamine], if contained in an aqueous solution, is susceptible to heat and is decomposed after exposing to heat for a long time. If an aqueous solution of free hydroxylamine, for example, is added at once to the reaction system, a large amount of water is present in early stages of the reaction. Thus, unreacted hydroxylamine is decomposed as a result of heating in the presence of such a large amount of water, and the yield of the cyclic N-hydroxyimide compound on the basis of hydroxylamine may often decrease. Consequently, an aqueous solution of free hydroxylamine is preferably fed to the reaction system consecutively (continuously or intermittently). In this connection, the amount of water in early stages of the reaction varies depending on the dewatering capability of the reaction system.

As a result of the reaction, a cyclic N-hydroxyimide compound corresponding to the reaction raw materials is formed. For example, the cyclic polycarboxylic acid anhydride represented by Formula (I), the polycarboxylic acid represented by Formula (II), or a mixture of them, if used as a raw material, yields a cyclic N-hydroxyimide compound represented by following Formula (III):

[Chemical Formula 7]

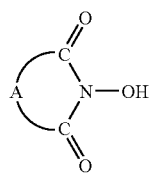
(III)

wherein A is as defined above.

After the completion of the reaction, the reaction product can be separated and purified, for example, by separation means such as filtration, concentration, extraction, crystallization, recrystallization or column chromatography, or a combination of these.

The process according to the present invention can produce cyclic N-hydroxyimide compounds in high yields from any of cyclic polycarboxylic acid anhydrides and polycarboxylic acids and significantly improve the utilization rate of the raw material component, as compared with conventional processes. These advantages are achieved probably for the following reasons. Taking the production of N-hydroxysuccinimide from succinic anhydride or succinic acid and hydroxylamine as an example, the reaction is supposed to proceed according to a reaction mechanism illustrated in the following scheme.

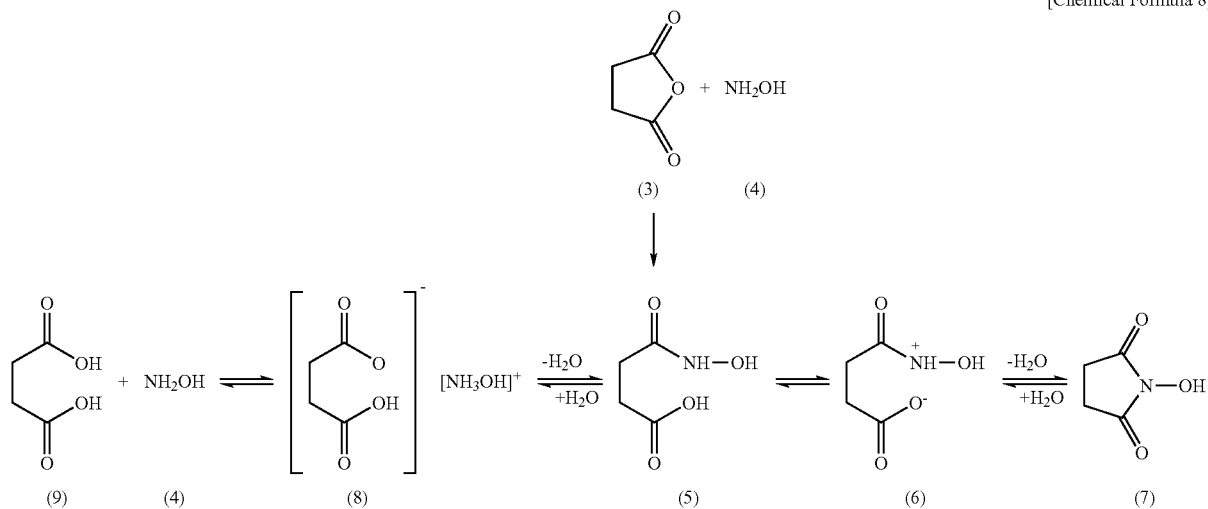

[Chemical Formula 8]

Upon the reaction of succinic anhydride (3) as a cyclic acid anhydride with hydroxylamine (4), succinic anhydride (3) initially undergoes ring opening to form a ring-opened product (5) having a carboxyl group at one end and a N-hydroxycarbamoyl group at the other. The two terminal groups of the ring-opened product (5) intramolecularly form an ammonium salt to form a compound (6), one water molecule then leaves the compound (6) to thereby form N-hydroxysuccinimide (7). If a large amount of water is present in the reaction system, the formed N-hydroxysuccinimide (7) undergoes reverse reaction with water and readily returns via the ammonium salt (6) to the ring-opened product (5). The ring-opened product (5) further reacts with water, forms an ammonium salt (8) of succinic acid and hydroxylamine and is decomposed to succinic acid (9) and hydroxylamine (4). Specifically, there are equilibria in the respective steps from succinic acid (9) to N-hydroxysuccinimide (7), and these equilibria govern the yield of N-hydroxysuccinimide (7). Probably for this reason, the use of an excessive amount of hydroxylamine (4) to succinic anhydride (3) improves the yield of N-hydroxysuccinimide (7) on the basis of succinic anhydride (3).

When succinic acid (9) which is a dicarboxylic acid corresponding to succinic anhydride (3) is used as the starting material, similar equilibria are established and the fundamental of the reaction is the same as the reaction using succinic anhydride (3). In the case of succinic acid (9) used as a starting material, the reactions to yield N-hydroxysuccinimide (7) by-produce water one molecule more than the case of succinic anhydride (3) used as a starting material, as illustrated in the scheme. Water serves to proceed the equilibria from the product to the raw materials. Consequently, a process using succinic acid (9) as a raw material is more disadvantageous for producing N-hydroxysuccinimide (7) than a process using succinic anhydride (3) as a raw material, from the viewpoint of reaction mechanism. This is because the former process by-produces water more than the latter process. Probably for this reason, most processes described in documents use a cyclic acid anhydride as a raw material and few employ a dicarboxylic acid.

In the process according to the present invention, however, the reaction is carried out while removing water from the reaction system, and the equilibria in the scheme move from the raw materials to the product. This probably contributes to high yield of a target cyclic N-hydroxyimide compound from any of a cyclic acid anhydride and a polycarboxylic acid used as the raw material.

One of preferred embodiments of the present invention is an embodiment comprising a first step of allowing a cyclic polycarboxylic acid anhydride, a polycarboxylic acid, or a mixture of them to react with hydroxylamine or a salt thereof in an organic solvent for predetermined time without dewatering, and second step of carrying out the reaction while conducting dewatering. This embodiment is typically advantageous when the produced cyclic N-hydroxyimide compound is used in the form of a solution in the organic solvent without isolation (e.g., when the organic solvent is used as a reaction solvent in a subsequent step) and the organic solvent is a solvent capable of forming a dehydration-condensation product with hydroxylamine.

Examples of the organic solvent capable of forming a dehydration-condensation product with hydroxylamine are aliphatic carboxylic acids such as formic acid, acetic acid, trifluoroacetic acid, propionic acid, butyric acid, isobutyric acid, valeric acid, hexanoic acid, heptanoic acid, octanoic acid, and decanoic acid; alicyclic carboxylic acids such as cyclohexanecarboxylic acid; and sulfonic acids such as methanesulfonic acid. Among them, monocarboxylic acids each having about one to about eight carbon atoms, preferably about one to about four carbon atoms, such as formic acid, acetic acid, and propionic acid, are preferred, of which aliphatic monocarboxylic acids are specifically preferred.

The reaction temperature in the first step is as the above-mentioned reaction temperature. The reaction time in the first step is, while varying depending typically on the species of the raw material components and organic solvent, generally about 0.5 to about 40 hours, preferably about 2 to about 25 hours, and more preferably about 5 to about 20 hours. It is preferred that the process moves to the second step at the time when the yield of the target cyclic N-hydroxyimide compound in the first step is maxing out and increases little. The reaction in the second step is as the above-mentioned reaction temperature. The reaction time in the second step is, while varying depending typically on the species of the raw material components and organic solvent, generally about 0.5 to about 40 hours, preferably about 1 to about 15 hours, and more preferably about 2 to about 10 hours.

According to this process, the formation of a reaction product between hydroxylamine and an organic solvent used as the reaction solvent is inhibited to thereby produce a target cyclic N-hydroxyimide compound in a good yield and to increase the utilization rate of hydroxylamine, even if hydroxylamine is reactive with the organic solvent. These advantages are obtained probably for the following reasons. Upon comparison between the target cyclic N-hydroxyimide compound formed from hydroxylamine with a polycarboxylic acid and a dehydration-condensation product of hydroxylamine with a reactive compound other than the polycarboxylic acid (e.g., a monocarboxylic acid such as acetic acid), in general, the former is stable with regard to free energy (with regard to thermodynamics) but the latter is advantageous with regard to enthalpy (with regard to kinetics). A chain N-hydroxy monoamide formed as a result of the reaction between hydroxylamine and a polycarboxylic acid is less thermodynamically stable than the target cyclic N-hydroxyimide compound but is more stable than a dehydration-condensation product between hydroxylamine and a reactive compound other than the polycarboxylic acid. Consequently, the dehydration-condensation product of hydroxylamine with a reactive compound other than the polycarboxylic acid is readily formed in early stages of the reaction, but the dehydration-condensation product is converted via the chain N-hydroxy monoamide into the target cyclic N-hydroxyimide compound with the passage of time. This reaction is an equilibrium reaction and requires the presence of water. If water is removed in early stages of the reaction, this equilibrium reaction does not proceed, and the dehydration-condensation product of hydroxylamine with a reactive compound other than the polycarboxylic acid (the reaction solvent in this case) remains in a considerable proportion. However, when the reaction is carried out without removing water from the reaction system in early stages of the reaction, and the dewatering procedure is started after the equilibrium reaction sufficiently proceeds, the amount of the produced dehydration-condensation product of hydroxylamine with the other reactive compound is small, and the target cyclic N-hydroxyimide compound can be efficiently produced.

This will be explained below with reference to the following scheme by taking the production of N-hydroxysuccinimide as a result of the reaction between succinic acid and hydroxylamine in acetic acid as a solvent. Succinic acid (9) reacts with hydroxylamine (4) to form a compound (5) (N-hydroxysuccinic acid monoamide) having a carboxyl group at one end and a N-hydroxycarbamoyl group at the other, and this compound in turn yields N-hydroxysuccinimide (7). Hydroxylamine (4) also reacts with acetic acid (10) as a solvent to form N-hydroxyacetic acid amide (11). The enthalpy ($\Delta H$) (kcal/mol) decreases in the order of $(9)+(4)+(10)>(7)>(11)>(5)$, and the free energy ($\Delta G$) (kcal/mol) decreases in the order of $(9)+(4)+(10)>(11)>(5)>(7)$. Specifically, target N-hydroxysuccinimide (7) is more thermodynamically stable than N-hydroxyacetic acid amide (11), but the latter is more readily formed than the former kinetically. Consequently, N-hydroxyacetic acid amide (11) is more readily formed in early stages of the reaction, and this compound is converted via the compound (5) into N-hydroxysuccinimide (7) with the passage of time. This reaction is an equilibrium reaction and requires the presence of water. If dewatering is conducted in early stages of the reaction, this equilibrium reaction does not proceed, and a considerable amount of N-hydroxyacetic acid amide (11) is obtained as a final product. However, by caring out the reaction through the first step of proceeding the reaction without dewatering and the second step of proceeding the reaction while carrying out dewatering as in the above-mentioned process, N-hydroxysuccinimide (7) can be efficiently produced while reducing the formation of N-hydroxyacetic acid amide (11).

[Chemical Formula 9]

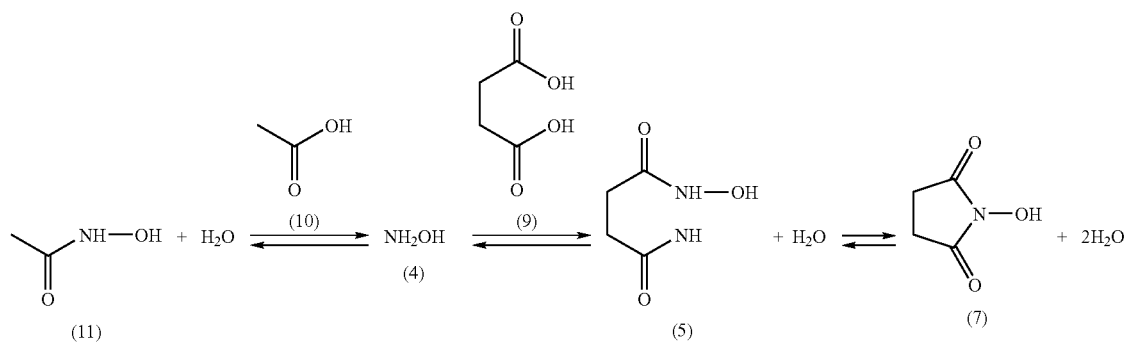

EXAMPLES

The present invention will be illustrated in further detail with reference to several examples below which by no means limit the scope of the present invention.

Example 1

In a 300-ml three-necked flask equipped with a Dean-Stark fractionating unit having an inner capacity of 20 ml and having a reflux condenser on its top, a thermometer, and a Teflon (registered trademark) mixing impeller as illustrated in FIG. 1 were placed 13.0 g of hydroxylamine hydrochloride, 22.0 g of potassium carbonate, 50 g of acetic acid, and 3.0 g of cyclohexane, and the Dean-Stark fractionating unit was filled with cyclohexane. The temperature was held at 65° C. on an oil bath. One hour later, 17.71 g of succinic acid was added to the mixture in the flask, and the temperature of the oil bath was raised until reflux began in the reflux condenser mounted to the top of the Dean-Stark. Heating was terminated eight hours later. Water by-produced in the reaction underwent azeotropy with cyclohexane, and the distillate cooled in the reflux condenser was separated into two layers, i.e., an organic layer and an aqueous layer in the Dean-Stark fractionating unit. The organic layer (cyclohexane layer) was recycled to the flask. The reaction mixture was analyzed by high-performance liquid chromatography (HPLC) to find to have a N-hydroxysuccinimide concentration of 16.4 percent by weight. This corresponds to a yield on the basis of succinic acid of 94.7%.

Comparative Example 1

In a 300-ml three-necked flask equipped with a reflux condenser, a thermometer and a Teflon (registered trademark) mixing impeller as illustrated in FIG. 2 were placed 13.0 g of hydroxylamine hydrochloride, 22.0 g of potassium carbonate, and 50 g of acetic acid, and the temperature was held at 65° C. on an oil bath. One hour later, 17.71 g of succinic acid was added to the mixture in the flask, and the temperature of the oil bath was raised until reflux began in the reflux condenser mounted to the flask. The reaction mixture was sampled and analyzed by HPLC every one hour to find that the concentration of N-hydroxysuccinimide stopped increasing five hours later and became constant thereafter. The concentration of N-hydroxysuccinimide at that time was 8.9 percent by weight. This corresponds to a yield on the basis of succinic acid of 10.4%.

Example 2

In a 300-ml three-necked flask equipped with a Dean-Stark fractionating unit having an inner capacity of 20 ml and having a reflux condenser on its top, a thermometer, and a Teflon (registered trademark) mixing impeller as illustrated in FIG. 1 were placed 37.41 g of a 50 percent by weight aqueous hydroxylamine solution, 150 g of acetic acid, 2.4 g of cyclohexane, and 53.1 g of succinic acid, and the Dean-Stark fractionating unit was filled with cyclohexane. The temperature of the oil bath was raised until reflux began in the reflux condenser mounted to the Dean-Stark. Heating was terminated six hours later. Water in the aqueous hydroxylamine solution and water by-produced as a result of the reaction underwent azeotropy with cyclohexane, and the distillate cooled in the reflux condenser was separated into two layers, i.e., an organic layer and an aqueous layer in the Dean-Stark fractionating unit. The organic layer (cyclohexane layer) was recycled to the flask. The reaction mixture was analyzed by HPLC to find to have a N-hydroxysuccinimide concentration of 13.4 percent by weight. This corresponds to a yield on the bases of succinic acid of 64.9%.

Example 3

In a 300-ml three-necked flask equipped with a Dean-Stark fractionating unit having an inner capacity of 20 ml and having a reflux condenser on its top, a thermometer, and a Teflon (registered trademark) mixing impeller as illustrated in FIG. 1 were placed 150 g of acetic acid, 2.4 g of cyclohexane, and 53.1 g of succinic acid, and the Dean-Stark fractionating unit was filled with cyclohexane. The temperature of the oil bath was raised until reflux began in the reflux condenser on the top of the Dean-Stark. Simultaneously with the beginning of reflux, a 50 percent by weight aqueous hydroxylamine solution was fed to the flask at a flow rate of 4.0 g per hour using a tubular constant rate pump. Heating was terminated nine hours later. Water in the aqueous hydroxylamine solution and water by-produced as a result of the reaction underwent azeotropy with cyclohexane, and the distillate cooled in the reflux condenser was separated into two layers, i.e., an organic layer and an aqueous layer in the Dean-Stark fractionating unit. The organic layer (cyclohexane layer) was recycled to the flask. The reaction mixture was analyzed by HPLC to find to have a N-hydroxysuccinimide concentration of 19.2 percent by weight. This corresponds to a yield on the basis of succinic acid of 91.9%.

Comparative Example 2

To a flask having an inner capacity of 100 ml of a reactor as illustrated in FIG. 2 were placed 12.34 g of a 50 percent by weight aqueous hydroxylamine solution, 50 g of acetic acid, and 17.71 g of succinic acid. The temperature of the oil bath was raised until reflux began in the reflux condenser mounted to the flask. The reaction mixture was sampled and analyzed by HPLC every one hour to find that the concentration of N-hydroxysuccinimide stopped increasing five hours later and became constant thereafter. The concentration of N-hydroxysuccinimide at that time was 4.5 percent by weight. This corresponds to a yield on the basis of succinic acid of 20.8%.

Example 4

In a flask having an inner capacity of 100 ml of a reactor equipped with a Dean-Stark fractioning column having an inner capacity of 10 ml as illustrated in FIG. 1 were placed 12.34 g of a 50 percent by weight aqueous hydroxylamine solution, 0.8 g of cyclohexane, 50 g of acetic acid, and 19.81 g of glutaric acid, and the Dean-Stark fractionating unit was filled with cyclohexane. The temperature of the oil bath was raised until reflux began in the reflux condenser mounted to the Dean-Stark. Heating was terminated five hours later. Water in the aqueous hydroxylamine solution and water by-produced as a result of the reaction underwent azeotropy with cyclohexane, and the distillate cooled in the reflux condenser was separated into two layers, i.e., an organic layer and an aqueous layer in the Dean-Stark fractionating unit. The organic layer (cyclohexane layer) was recycled to the flask. The reaction mixture was analyzed by HPLC to find to have a N-hydroxyglutarimide concentration of 4.9 percent by weight. This corresponds to a yield on the basis of glutaric acid of 36.7%.

Comparative Example 3

The procedure of COMPARATIVE EXAMPLE 2 was repeated, except for using 19.81 g of glutaric acid instead of 17.71 g of succinic acid. The concentration of N-hydroxyglurarimide stopped increasing six hours later and became constant thereafter. The concentration of N-hydroxyglurarimide at that time was 3.0 percent by weight. This corresponds to a yield on the basis of glutaric acid of 12.9%.

Example 5

The procedure of EXAMPLE 2 was repeated, except for using 21.92 g of adipic acid instead of 19.81 g of glutaric acid used in EXAMPLE 4. The concentration of N-hydroxyadipimide in the reaction mixture sampled eight hours later was 2.9 percent by weight. This corresponds to a yield on the basis of adipic acid of 19.7%.

Comparative Example 4

The procedure of COMPARATIVE EXAMPLE 2 was repeated, except for using 21.92 g of adipic acid instead of 17.71 g of succinic acid. The concentration of N-hydroxyadipimide stopped increasing six hours later and became constant thereafter. The concentration of N-hydroxyglurarimide at that time was 0.8 percent by weight. This corresponds to a yield on the basis of glutaric acid of 5.4%.

Example 6

In a flask having an inner capacity of 100 ml of a reactor equipped with a Dean-Stark fractioning column having an inner capacity of 10 ml as illustrated in FIG. 1 were placed 12.34 g of a 50 percent by weight aqueous hydroxylamine solution, 50 g of xylene, and 17.71 g of succinic acid, and the Dean-Stark fractionating unit was filled with xylene. The temperature of the oil bath was raised until reflux began in the reflux condenser mounted to the Dean-Stark. Heating was terminated eight hours later. Water in the aqueous hydroxylamine solution and water by-produced in the reaction underwent azeotropy with xylene, and the distillate cooled in the reflux condenser was separated into two layers, i.e., an organic layer and an aqueous layer in the Dean-Stark fractionating unit. The organic layer (xylene layer) was recycled to the flask. The reaction mixture was cooled to room temperature, and a solid was precipitated. The solid was filtrated, was dried at 55° C. in vacuo and was weighed to find that the weight was 14.2 g. The concentration of N-hydroxysuccinimide in this solid was analyzed by HPLC to find to be 48.7 percent by weight. This corresponds to a yield on the basis of succinic acid of 40.4%.

Comparative Example 5

In a flask having an inner capacity of 100 ml of a reactor as illustrated in FIG. 2 were placed 12.34 g of a 50 percent by weight aqueous hydroxylamine solution, 50 g of xylene, and 17.71 g of succinic acid. The temperature of the oil bath was raised until reflux began in the reflux condenser mounted to the flask. The reaction mixture was sampled and analyzed by HPLC every one hour to find that the concentration of N-hydroxysuccinimide stopped increasing eight hours later and became constant thereafter. The reaction mixture was cooled to room temperature, and a solid was precipitated. The solid was filtrated, was dried at 55° C. in vacuo and was weighed to find that the weight was 13.23 g. The concentration of N-hydroxysuccinimide in this solid was analyzed by HPLC to find to be 9.6 percent by weight. This corresponds to a yield on the basis of succinic acid of 7.1%.

Example 7

In a flask equipped with a Dean-Stark fractionating unit were placed 10 g of pyromellitic anhydride, 90 g of acetic acid, and 20 g of hexane, and the mixture was heated on a bath at 100° C. After checking that reflux began and the temperature of the reaction mixture reached 74° C., 6.66 g of a 50 percent by weight aqueous hydroxylamine solution was added dropwise. The mixture was stirred for two hours while controlling its temperature to a range from 70° C. to 74° C. and removing water. The reaction mixture was analyzed by HPLC to find that N,N'-dihydroxypyromellitic diimide was produced in a yield of 70% with a conversion from pyromellitic anhydride of 80%.

Comparative Example 6

In a flask were placed 10 g of pyromellitic anhydride and 90 g of acetic acid, and the mixture was heated on a bath at 80° C. After the temperature of the mixture reached 77° C., 6.66 g of a 50 percent by weight aqueous hydroxylamine solution was added dropwise. The mixture was stirred for two hours while controlling the temperature thereof to a range from 77° C. to 80° C. The reaction mixture was analyzed by HPLC to find that N,N'-dihydroxypyromellitic diimide was produced in a yield of 42% with a conversion from pyromellitic anhydride of 70%.

Example 8

A 200-ml three-necked flask was equipped with a pump for feeding acetic acid, a liquid-level meter, and a Dean-Stark fractionating unit. The Dean-Stark fractionating unit was equipped with a pump for liquid extraction. The liquid-level meter ganged with the pump for feeding acetic acid and was so configured as to keep the liquid level in the flask constant by feeding acetic acid.

In the flask were placed 54.9 g of acetic acid, and 50.8 g of a salt between hydroxylamine and succinic acid (a 1:1 salt of hydroxylamine and succinic acid), and the mixture was held under reflux for ten hours. The content in the reactor was analyzed by HPLC at this point of time to find that N-hydroxysuccinimide and N-hydroxyacetamide were produced in yields of 70.1% and 9.8%, respectively. The pump mounted to the Dean-Stark fractionating unit was then set in motion so as to extract the mixture in the fractionating unit at a rate of 10 g per hour, and the pump for feeding acetic acid was also set in motion so as to keep the liquid level in the flask constant. The content in the reactor was analyzed by HPLC five hours later to find that N-hydroxysuccinimide and N-hydroxyacetamide were produced in yields of 94.6% and 3.7%, respectively.

Comparative Example 7

The same amounts of acetic acid and the salt between hydroxylamine and succinic acid as EXAMPLE 8 were placed in the same reactor as EXAMPLE 8, and the mixture was held under reflux. At the beginning of reflux, the pump mounted to the Dean-Stark fractionating unit was set in motion to extract the mixture in the fractionating unit at a rate of 10 g per hour, and the pump for feeding acetic acid was also set in motion to keep the liquid level in the flask constant. Ten hours later the content in the reactor was analyzed by HPLC to find that N-hydroxysuccinimide and N-hydroxyacetamide were produced in yields of 54.4% and 44.5%, respectively.

INDUSTRIAL APPLICABILITY

According to the present invention, cyclic N-hydroxyimide compounds can be produced in good yields from any of cyclic polycarboxylic acid anhydrides and polycarboxylic acids, and the utilization rate of the raw material component can be significantly improved. The resulting cyclic N-hydroxyimide compounds are useful typically as oxidizing agents for use in developers for photographs, reagents for synthetically preparing peptides, oxidizing catalysts, intermediates for synthetically preparing insecticides, and initiators for polymerization reactions.

The invention claimed is:

1. A process for producing cyclic N-hydroxyimide compounds, the process comprising:
    a first step of allowing a cyclic polycarboxylic acid anhydride, a polycarboxylic acid, or a mixture of them to react with hydroxylamine or a salt thereof in an organic solvent for predetermined time without dewatering; and
    after the first step, a second step of allowing a cyclic polycarboxylic acid anhydride, a polycarboxylic acid, or a mixture of them to react with hydroxylamine or a salt thereof in the organic solvent while carrying out dewatering,
    wherein the organic solvent is capable of forming a dehydration-condensation product with hydroxylamine, and the organic solvent is a monocarboxylic acid having one to eight carbon atoms.

2. The process for producing cyclic N-hydroxyimide compounds according to claim 1, wherein the organic solvent is carboxylic acids.

3. The process for producing cyclic N-hydroxyimide compounds according to claim 1, wherein the cyclic polycarboxylic acid anhydride is a compound represented by the following Formula (1):

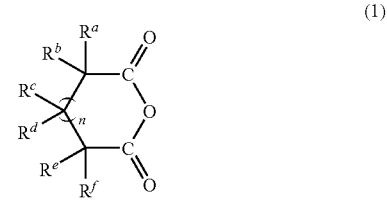

(1)

wherein $R^a$, $R^b$, $R^c$, $R^d$, $R^e$ and $R^f$ are the same as or different from one another and each represents a hydrogen atom, a halogen atom, an alkyl group, a haloalkyl group, an aryl group, an aralkyl group, a cycloalkyl group, a hydroxyl group, an alkoxy group, carboxyl group, a substituted oxycarbonyl group, a substituted or unsubstituted carbamoyl group, an acyl group, an acyloxy group, sulfo group, a substituted oxysulfonyl group, a substituted or unsubstituted sulfamoyl group, nitro group, a substituted or unsubstituted amino group, a substituted or unsubstituted phosphono group, or a substituted or unsubstituted phosphonooxy group, wherein at least two of $R^a$, $R^b$, $R^c$, $R^d$, $R^e$ and $R^f$ optionally combine to form a double bond with an adjacent carbon-carbon bond or to form an aromatic or non-aromatic ring with an adjacent carbon atom or carbon chain, and wherein the compound may have two or more cyclic acid anhydride skeletons per molecule; and n denotes 0, 1 or 2.

4. The process for producing cyclic N-hydroxyimide compounds according to claim 1, wherein the cyclic polycarboxylic acid anhydride is at least one compound selected from the group consisting of succinic anhydride, glutaric anhydride, phthalic anhydride, trimellitic anhydride, pyromellitic monoanhydride, pyromellitic dianhydride, 1,8-naphthalenedicarboxylic anhydride, 2,3-naphthalenedicarboxylic anhydride, 1,4,5,8-naphthalenetetracarboxylic monoanhydride, 1,4,5,8-naphthalenetetracarboxylic dianhydride, 2,3,6,7-naphthalenetetracarboxylic monoanhydride, and 2,3,6,7-naphthalenetetracarboxylic dianhydride.

5. The process for producing cyclic N-hydroxyimide compounds according to claim 1, wherein the polycarboxylic acid is a compound represented by following Formula (2):

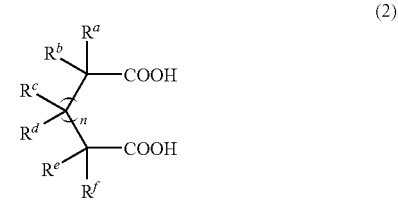

(2)

wherein $R^a$, $R^b$, $R^c$, $R^d$, $R^e$ and $R^f$ are the same as or different from one another and each represents a hydrogen atom, a halogen atom, an alkyl group, a haloalkyl group, an aryl group, an aralkyl group, a cycloalkyl group, a hydroxyl group, an alkoxy group, carboxyl group, a substituted oxycarbonyl group, a substituted or unsubstituted carbamoyl group, an acyl group, an acyloxy group, sulfo group, a substituted oxysulfonyl group, a substituted or unsubstituted sulfamoyl group, nitro group, a substituted or unsubstituted amino group, a substituted or unsubstituted phosphono group, or a substituted or unsubstituted phosphonooxy group, wherein at least two of $R^a$, $R^b$, $R^c$, $R^d$, $R^e$ and $R^f$ optionally combine to form a double bond with an adjacent carbon-carbon bond or to form an aromatic or non-aromatic ring with an adjacent carbon atom or carbon chain, and wherein the compound may have two or more pairs of carboxyl groups capable of forming a cyclic imide skeleton per molecule; and n denotes 0, 1 or 2.

6. The process for producing cyclic N-hydroxyimide compounds according to claim 1, wherein the polycarboxylic acid is at least one compound selected from the group consisting of succinic acid, glutaric acid, adipic acid, phthalic acid, trimellitic acid, pyromellitic acid, 1,8-naphthalenedicarboxylic acid, 2,3-naphthalenedicarboxylic acid, 1,4,5,8-naphthalenetetracarboxylic acid, and 2,3,6,7-naphthalenetetracarboxylic acid.

7. The process for producing cyclic N-hydroxyimide compounds according to claim 1, wherein the amount of said organic solvent is 10 to 5000 parts by weight to 100 parts by weight of the total of said cyclic polycarboxylic acid anhydride and said polycarboxylic acid used in the reaction.

8. The process for producing cyclic N-hydroxyimide compounds according to claim 1, further comprising carrying out the reaction while continuously or intermittently adding an aqueous hydroxylamine solution to the reaction system.

9. A process for producing cyclic N-hydroxyimide compounds, the process comprising:
a first step of allowing a polycarboxylic acid or a mixture of the polycarboxylic acid and a cyclic polycarboxylic acid anhydride to react with free hydroxylamine in an organic solvent for predetermined time without dewatering; and
after the first step, a second step of allowing a polycarboxylic acid or a mixture of the polycarboxylic acid and a cyclic polycarboxylic acid anhydride to react with free hydroxylamine in the organic solvent while carrying out dewatering,
wherein the organic solvent is capable of forming a dehydration-condensation product with hydroxylamine and the organic solvent is a monocarboxylic acid having one to eight carbon atoms.

10. The process for producing cyclic N-hydroxyimide compounds according to claim 9, further comprising carrying out the reaction while continuously or intermittently adding an aqueous hydroxylamine solution containing the free hydroxylamine to the reaction system.

11. The process for producing cyclic N-hydroxyimide compounds according to claim 9, wherein the amount of said organic solvent is 10 to 5000 parts by weight to 100 parts by weight of the total of said cyclic polycarboxylic acid anhydride and said polycarboxylic acid used in the reaction.

\* \* \* \* \*